US009389165B2

(12) United States Patent
Fulghum et al.

(10) Patent No.: US 9,389,165 B2
(45) Date of Patent: Jul. 12, 2016

(54) SYSTEM RESPONSIVE TO MACHINE VIBRATIONS AND METHOD OF USE

(71) Applicant: Virtjoule, Inc., Monument, CO (US)

(72) Inventors: Craig A. Fulghum, Rolle (CH); Randall R. Cox, Niwot, CO (US); Landon J. Cox, Monument, CO (US)

(73) Assignee: VIRTJOULE, INC., Monument, CO (US)

( * ) Notice: Subject to any disclaimer, the term of this patent is extended or adjusted under 35 U.S.C. 154(b) by 835 days.

(21) Appl. No.: 13/677,173

(22) Filed: Nov. 14, 2012

(65) Prior Publication Data

US 2013/0073228 A1 Mar. 21, 2013

Related U.S. Application Data

(63) Continuation-in-part of application No. 13/529,742, filed on Jun. 21, 2012.

(60) Provisional application No. 61/500,141, filed on Jun. 23, 2011.

(51) Int. Cl.
| | |
|---|---|
| *G01H 17/00* | (2006.01) |
| *G01D 21/00* | (2006.01) |
| *G01M 13/00* | (2006.01) |
| *G08C 25/00* | (2006.01) |
| *G06F 17/40* | (2006.01) |
| *G06F 19/00* | (2011.01) |
| *G01N 19/00* | (2006.01) |
| *G06F 15/00* | (2006.01) |
| *G05B 19/418* | (2006.01) |

(Continued)

(52) U.S. Cl.
CPC ............ *G01N 19/00* (2013.01); *G01D 21/00* (2013.01); *G01H 17/00* (2013.01); *G01M 13/00* (2013.01); *G05B 15/02* (2013.01); *G05B 19/4184* (2013.01); *G05B 23/0224* (2013.01); *G06F 15/00* (2013.01); *G08C 25/00* (2013.01); *G05B 2219/2614* (2013.01); *G05B 2219/31205* (2013.01); *G05B 2219/37435* (2013.01); *G06F 17/40* (2013.01); *G06F 19/00* (2013.01); *Y02P 90/14* (2015.11); *Y02P 90/18* (2015.11)

(58) Field of Classification Search
None
See application file for complete search history.

(56) References Cited

U.S. PATENT DOCUMENTS

| | | | | |
|---|---|---|---|---|
| 3,242,321 | A * | 3/1966 | Chope | G07C 3/005 131/910 |
| 4,520,674 | A * | 6/1985 | Canada | G01H 1/00 702/197 |
| 5,726,911 | A * | 3/1998 | Canada | G01R 31/343 318/434 |

(Continued)

*Primary Examiner* — Edward Cosimano
(74) *Attorney, Agent, or Firm* — Michael E. Broms; Berenbaum Weinshienk PC (57) ABSTRACT

A first embodiment of a system for measuring and analyzing a machine property includes a detector with a vibration sensor, power source, a data transmitter, a first data processor configured and adapted to obtain sensed vibration data from the sensor and convert it into digital data to be transmitted through the data transmitter, and a system server operatively in communication with the detector. The system server has software that can process and analyze data such as the sensed vibration data received via the data receiver. In a second embodiment, the system includes a vibration sensor, a terminal comprising a user interface unit and a first data processor that can obtain sensed vibration data from the sensor and convert it into digital data to be transmitted through the first data transceiver. In this embodiment, data may be presented visually on the user display area and user input received input from the user input area.

19 Claims, 12 Drawing Sheets

(51) Int. Cl.
*G05B 15/02* (2006.01)
*G05B 23/02* (2006.01)

(56) References Cited

U.S. PATENT DOCUMENTS

| | | | | |
|---|---|---|---|---|
| 5,847,658 A * | 12/1998 | Irie | ............... | G01H 1/00 340/683 |
| 5,852,351 A * | 12/1998 | Canada | ............... | G01R 31/343 318/490 |
| 5,854,994 A * | 12/1998 | Canada | ............... | G01H 1/003 340/3.63 |
| 5,870,699 A * | 2/1999 | Canada | ............... | G01H 1/14 702/113 |
| 5,907,491 A * | 5/1999 | Canada | ............... | G01H 1/003 340/3.1 |
| 5,952,803 A * | 9/1999 | Canada | ............... | G01R 31/343 318/558 |
| 5,963,884 A * | 10/1999 | Billington | ............... | G21C 17/00 702/56 |
| 6,138,078 A * | 10/2000 | Canada | ............... | G01R 31/343 318/490 |
| 6,297,742 B1 * | 10/2001 | Canada | ............... | G01R 31/343 318/490 |
| 6,301,514 B1 * | 10/2001 | Canada | ............... | G01H 1/003 340/3.1 |
| 6,671,633 B2 * | 12/2003 | Kramb | ............... | G01M 15/14 702/189 |
| 8,442,688 B2 * | 5/2013 | Loutfi | ............... | F27B 7/42 366/1 |
| 8,810,396 B2 * | 8/2014 | Hedin | ............... | G01H 1/003 340/540 |
| 8,868,242 B2 * | 10/2014 | Loutfi | ............... | F27B 7/42 700/17 |
| 9,176,003 B2 * | 11/2015 | Sun | ............... | G01H 1/003 |
| 9,229,438 B2 * | 1/2016 | Fulghum | ............... | G05B 15/02 |
| 2003/0212504 A1 * | 11/2003 | Kramb | ............... | G01M 15/14 702/34 |
| 2011/0184547 A1 * | 7/2011 | Loutfi | ............... | F27B 7/42 700/110 |
| 2011/0285532 A1 * | 11/2011 | Hedin | ............... | G01M 13/045 340/540 |
| 2011/0291850 A1 * | 12/2011 | Sun | ............... | G01H 1/003 340/683 |
| 2012/0330579 A1 * | 12/2012 | Fulghum | ............... | G05B 23/0224 702/56 |
| 2013/0323127 A1 * | 12/2013 | Loutfi | ............... | F27B 7/42 422/119 |

* cited by examiner

SYSTEM RESPONSIVE TO MACHINE VIBRATIONS AND METHOD OF USE

CROSS-REFERENCE TO RELATED APPLICATION

This application is a continuation-in-part of U.S. Utility application Ser. No. 13/529,742, filed Jun. 21, 2012, now U.S. Pat. No. 9,229,438, which claims priority to and the benefit of U.S. Provisional Application No. 61/500,141 filed Jun. 23, 2011.

BACKGROUND

Typical monitoring systems are integrated with a building automation system and installed by a Heating/Ventilation/Air Conditioning ("HVAC") expert. Installation often involves installation of multiple, e.g. five or more, sensors installed inside the machine to measure temperatures and pressures. This process is often expensive and time consuming.

A need exists for relatively low cost sensor systems that can be installed by a layperson, including systems that comprise multiple processes and components that enable a layperson to perform real-time problem diagnosis and continuous monitoring of complex machinery.

DRAWINGS

The figures supplied herein disclose various embodiments of the claimed invention.

DETAILED DESCRIPTION OF EMBODIMENTS

In its various embodiments, the system obtains vibration and optionally other signals and takes advantage of both localized and distributed analysis as well as localized data (e.g. climate data, building management system data etc.) to detect machine faults or other suboptimal operating characteristics.

Figure 1:
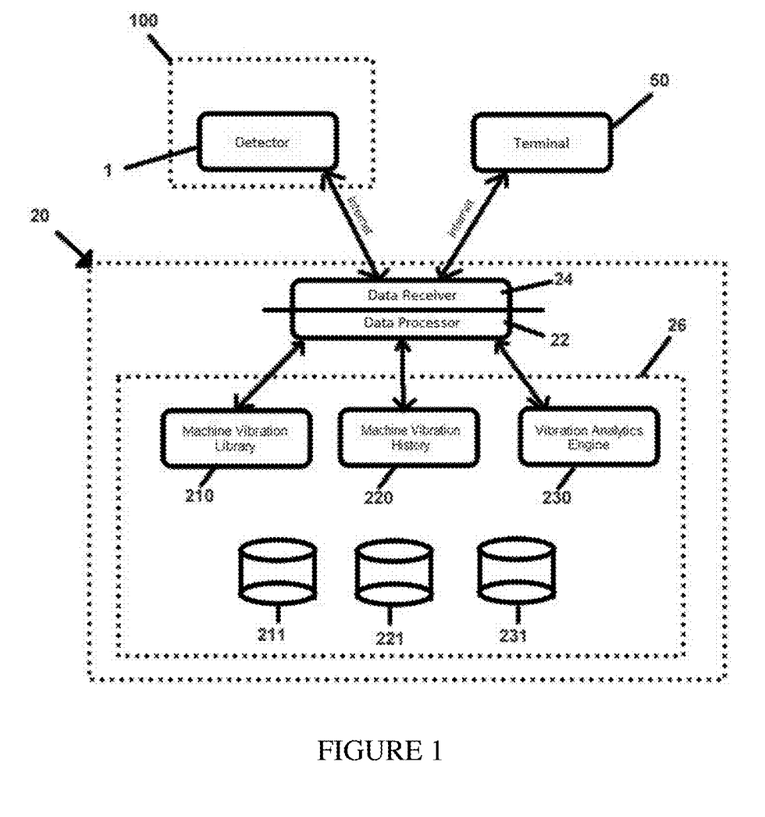
FIG. 1 is a block diagram illustrating examples of the machine vibration linking components.
Figure 2:
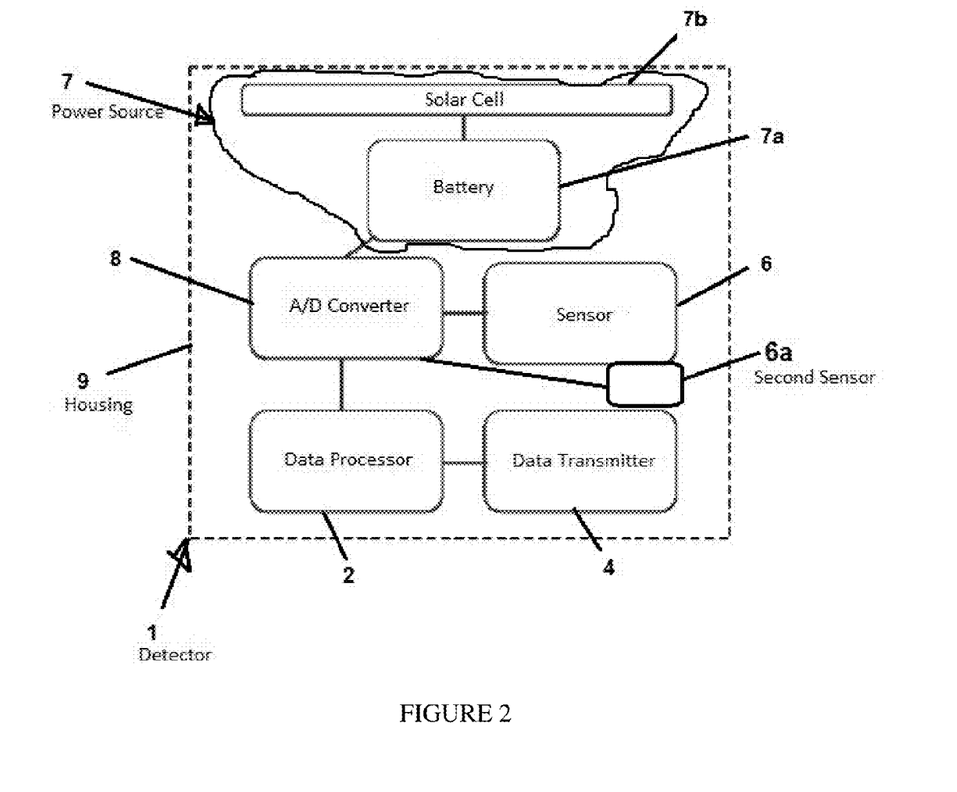
FIG. 2 is a block diagram illustrating machine vibration linking applications.

Referring now to FIGS. 1 and 2, in a first embodiment a system for measuring and analyzing a machine property comprises detector 1 and system server 20. FIG. 1 illustrates how various components may be connected through wired or wireless methods, e.g. via the Internet, using cellular technology, Ethernet, wireless, optical, radio transmission, or the like, or a combination thereof. As used herein, "machine property" includes vibration and may include other properties such as temperature, power usage, and the like, or combinations thereof.

In an embodiment, detector 1 further comprises power source 7 (which can include components 7a and 7b, as further discussed herein below); sensor 6 operatively connected to power source 7; data transmitter 4 operatively connected to power source 7; and first data processor 2 operatively connected to sensor 6, power source 7, and data transmitter 4.

In some embodiments, power source 7 can comprise battery 7a, solar cell 7b, or the like, or a combination thereof, where battery 7a may be further connected to solar cell 7b.

Data transmitter 4 can be a one-way transmitter or a two-way data transceiver. In either configuration, data transmitter 4 may transmit via a wired connection, a wireless connection, or the like, or a combination thereof. In this instance, wired and wireless include electromagnetic as well as acoustic or light energy.

Sensor 6 is typically dimensioned and configured to sense vibration of structural component 100 with which sensor 6 is operatively in contact. In currently envisioned embodiments, sensor 6 comprises a vibration transducer, a piezoelectric sensor, a microphone, an acoustic microphone, an accelerometer, or the like, or a combination thereof. First data processor 2 is typically configured and adapted to obtain at least sensed vibration data from sensor 6 and convert it into digital data to be transmitted through data transmitter 4.

In certain embodiments, detector 1 comprises second sensor 6a operatively connected to first data processor 2. Second sensor 6a is typically configured and dimensioned to sense a predetermined second physical characteristic relative to structural component 100. In currently contemplated embodiments, second sensor 6a may comprise a piezoelectric detector, a thermal imaging detector, a current sensor, a voltage sensor, a microphone, an acoustic microphone, an accelerometer, or the like, or a combination thereof. By way of example and not exclusion, second sensor 6a may comprise a current and/or voltage transducer operatively connected to a power line (not shown) leading to structural component 100. In such embodiments, the predetermined second physical characteristic may comprise sensed voltage and/or current in the power line and first data processor 2 is further configured and adapted to obtain the sensed voltage and/or current in the power line and convert it into data to be transmitted through data transmitter 4. By way of further example and not exclusion, the predetermined second physical characteristic may be a raw signal voltage, a signal FFT, a signal strength, a decibel level, a signal pattern, a GPS location, local realtime/historic climate data, temperature, wind direction/speed, humidity, a weather condition, a whole building measurement, a unit electric measurement, a natural gas measurement, an inside space condition, a thermostat function, a thermostat history, or the like, or a combination thereof.

System server 20 is operatively in communication with detector 1 and further comprises second data processor 22; data receiver 24 operatively connected to second data processor 22; and software (e.g., 210 and 230) operatively resident in data store 26 which is operatively in communication with second data processor 22, e.g. a hard drive, an optical drive, RAM, ROM, or the like, or a combination thereof. System server 20 may comprise one or more personal computers, embedded computers, personal digital assistants, or the like and the included computers may be standalone or networked. The software is dimensioned and configured to process and analyze data comprising the sensed vibration data received via data receiver 24.

Figure 3:
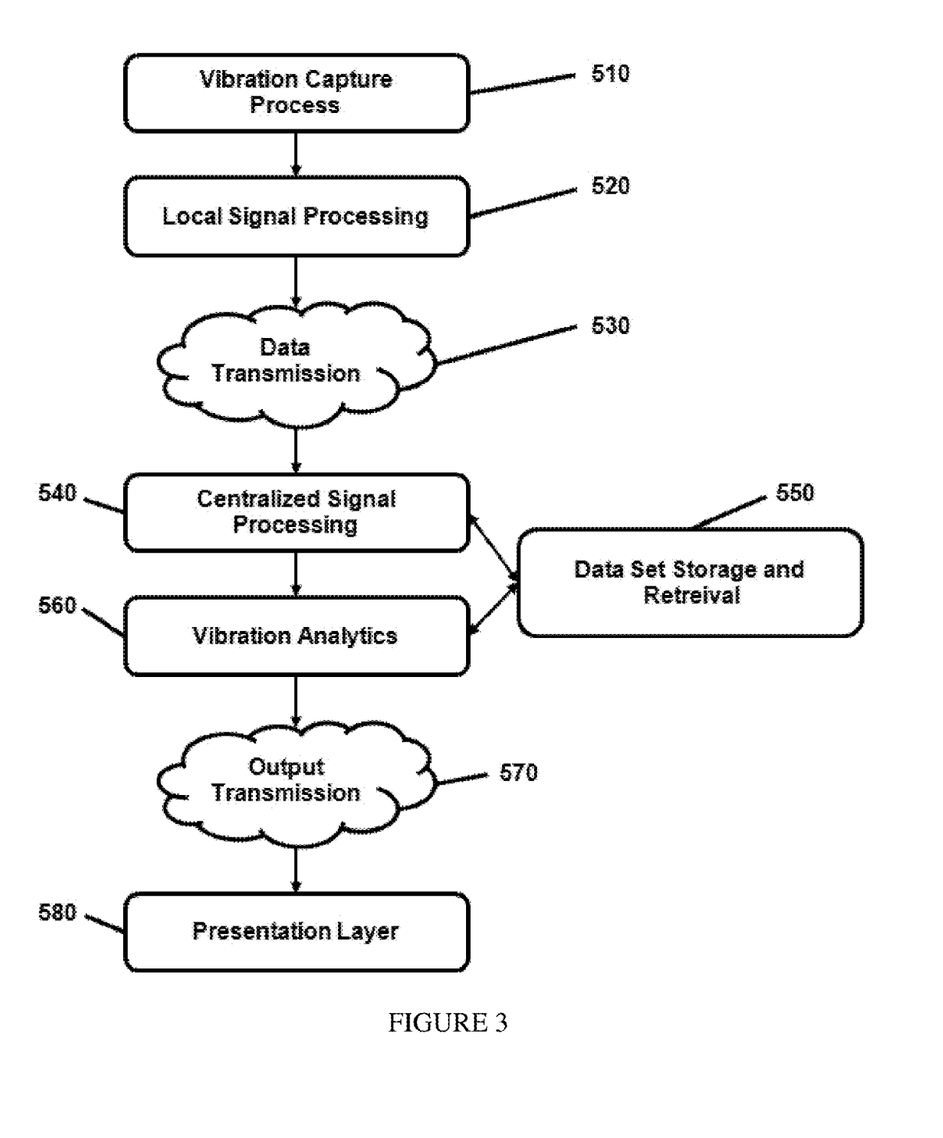
FIG. 3 is a flow diagram illustrating implementation of invention.

Data store 26 typically comprises historical vibration database 221, realtime vibration database 231, vibration fault library 210, or the like, or a combination thereof. Vibration data can be stored in one or more of these databases. Vibration data may also be stored in machine vibration history 220 which is operatively in communication with second data processor 22. Processed data may be stored in vibration fault library 210 for utilization in the vibration analytics process (FIG. 1 and FIG. 3). Vibration analytics can use a variety of techniques to determine the performance and relevance of the machine vibration. These techniques may include statistical techniques utilizing historical, comparative (similar machines, faults, etc) realtime or simulated data sets. The statistical techniques may include but are not limited to basic regression analysis, pattern recognition, Bayesian networks, etc. These techniques may or may not use referenced data sets to determine machine performance. In addition, other numerical analysis methods can be used. (FIG. 1 and FIG. 3).

Detector 1 may be configured and dimensioned as a selectively detachable device, a permanently attached device, a device externally mountable to structural component 100, a device externally mountable to structural component 100, a selectively embedded device, or a permanently embedded device as well as a hardwired device that may be incorporated into these systems and devices. The mobile device may capture analog vibration through existing embedded sensors (microphone, accelerometer, etc) typically found on mobile devices such as smart phones or may utilize additional inputs/hardware attached to the device such as an external sensor (accelerometer, microphone, piezio electric transducer, etc). In addition the vibration input may be subjected to amplification devices.

In other configurations, detector 1 may further comprise A/D converter 8 operatively in communication with sensor 6 or sensor 6a and first data processor 2. Detector 1 may further comprise an amplifier (not shown) operatively connected to sensor 6 and/or sensor 6a where the amplifier is adapted to amplify the information received by sensor 6 and/or sensor 6a.

Figure 11:
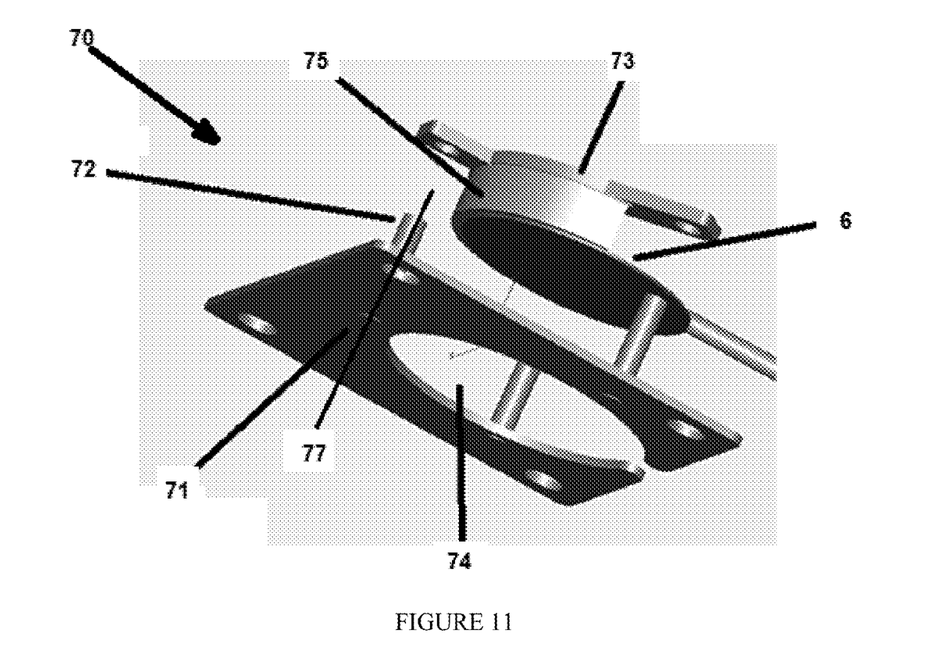
FIG. 11 is a view in partial perspective of a sensor assembly illustrating a sensor platform, sensor, and sensor mount.
Figure 12:
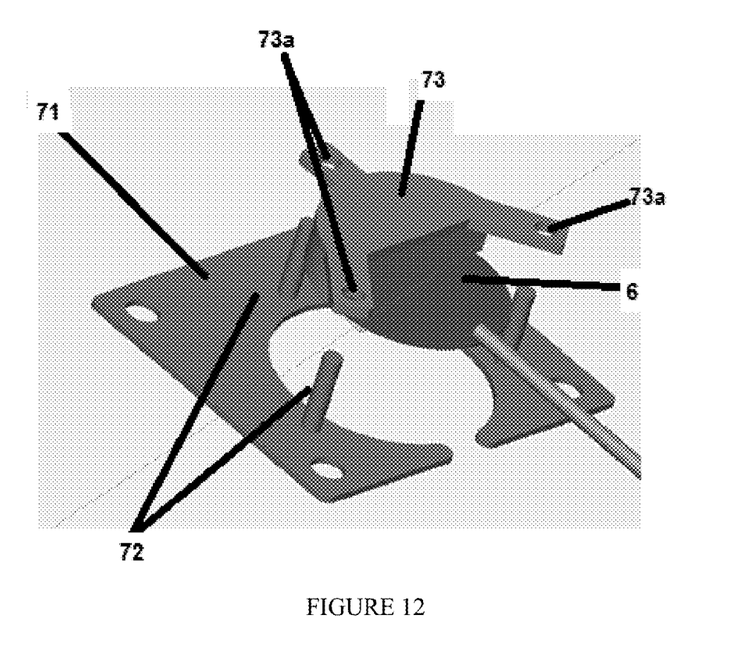
FIG. 12 is a further view in partial perspective of the sensor assembly illustrating a sensor platform, sensor, and sensor mount.
Figure 13:
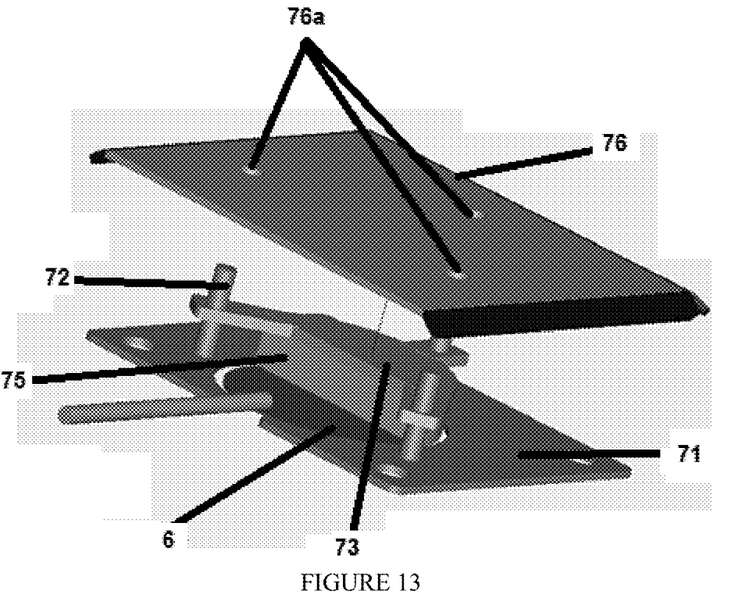
FIG. 13 is a further view in partial perspective of the sensor assembly illustrating a sensor platform, sensor, and sensor mount.

In other configurations, detector 1 may further comprise housing 9 where power source 7, sensor 6, data transmitter 4, and first data processor 2 are at least partially disposed within housing 9. Referring additionally to FIGS. 11-13, in certain of these embodiments, detector 1 includes sensor assembly 70 which comprises sensor platform 71, one or more guides 72 which are connected to sensor platform 71, and sensor mount 73 which is typically dimensioned to be slidingly engaged along guides 72.

Sensor platform 71 is dimensioned to selectively receive sensor 6 and is further configured to be either substantially non-removably or substantially removably secured to structural component 100 FIG. 1) such as by using screws, adhesive glue, or tape, or the like, or a combination thereof, attached to a predetermined portion of sensor platform 71. Sensor 6 typically comprises a predetermined exterior shape, e.g. a substantially circular circumference, although other shapes may be used, and sensor platform 71 comprises a cooperatively shaped void 74 configured to receive sensor 6 so as to allow positioning of sensor 6 to a desired position relative to structural component 100 and maintaining that position. Sensor platform 71 and/or cover and cover 76 (FIG. 13) may comprise an appropriate metal such as steel or 050 aluminum, an ABS plastic, or the like, or a combination thereof, the material being selected to be appropriate for its intended environmental placement, provided that it provides a stiffness such that forces applied will neither warp nor displace sensor platform 71, sensor mount 73, or cover plate 76.

Guides 72 optionally comprise tubular posts, and guide 72 and sensor mount 73 are configured to cooperatively guide sensor 6 into sensor assembly or housing 70, e.g. along one or more axes defined by guides 72. In one embodiment, sensor mount 73 comprises annulus 73a dimensioned to allow guide 72 to pass through annulus 73a. In a further embodiment, each guide 72 has a corresponding annulus 73a. However, guides 72 need not be tubular and can be of any appropriate shape.

In most embodiments, sensor mount 73 is guided by guides 72 in such a manner as to be able to move up and down the posts more or less freely, generally toward sensor platform 71.

In certain embodiments, cushion 75 may be present and configured to connect to and cushion sensor 6, e.g. be disposed between sensor 6 and sensor mount 73. Cushion 75 may comprise a foam, a rubber, a gel, or the like, or a combination thereof, and may further be attached to either or both of sensor 6 or sensor mount 73 such as with an appropriate glue. Cushion 75 therefore typically comprises a material is that is firm enough to apply pressure to sensor 6 and hold cushion 75 against sensor 6 for a long period of time, such as rubber. Attachment of cushion 75 to sensor mount 73 and/or attachment of cushion 75 to sensor 6 may also be accomplished using double sided mounting tape, building silicone, soft forms of hot glue, and the like, or a combination thereof. In certain contemplated embodiments, no adhesive may be required such as when using cushion 75 in the field, e.g. cushion 75 may be held in place by using pressure applied to cushion 75.

In further embodiments, sensor assembly 70 further comprises cover 76 which may be connected to sensor platform 71. Cover 76 is typically dimensioned to substantially cover sensor 6. In other embodiments, cover 76 may cover substantially all of sensor assembly 70 and/or substantially all of detector 1 (FIG. 2). Cover 76 typically comprises a set of cooperatively dimensioned guide receivers 76a which are dimensioned to correspond to guides 72. Cover 76 is typically configured to be secured to guide 72 using a selectively removable fastener in communication with guide 72 such as a thumb nut, wing nut, friction washer or screw, or the like, or a combination thereof. In some configurations, guide 72 comprises a threaded stud or machine screw.

Cover 76 is typically dimensioned to apply pressure to sensor mount 73 and keep sensor mount 73 in place when sensor mount 73 is in a desired position. Typically, the selectively removable fastener applies pressure on cover 76 which, in turn, applies pressure to sensor mount 73 and/or cushion 75. In these embodiments, guide 72, e.g. threaded guide 72, is used to apply downward pressure on sensor mount 73, transferring a soft pressure through cushion 75 onto sensor 6.

In certain embodiments, terminal 50 is operatively in communication with detector 1 and/or system server 20. Terminal 50 may be a personal computer, a smart phone, a mobile phone, a personal digital assistant (PDA), a dedicated mobile device, a tablet computing device, or the like. Terminal 50 is typically operatively in communication with server system 20 and further adapted and configured to receive a request from a user.

In addition to the above described embodiment, other embodiments exist that are responsive to machine vibrations. One additional embodiment exists where all processes and databases reside on a mobile device, e.g. terminal 50 (FIG. 7), or a dedicated embedded device, e.g. detector 1. In another embodiment, a majority of processing occurs locally, e.g. terminal 50 and/or detector 1 (FIG. 7), but the local device is connected via the Internet to, e.g. system server 20 which processes the data and directs the output to an end user. Other, additional embodiments exist wherein one or more processes, such as those outlined in FIG. 3, are removed from the process but still provide the required performance information to the end user.

Figure 7:
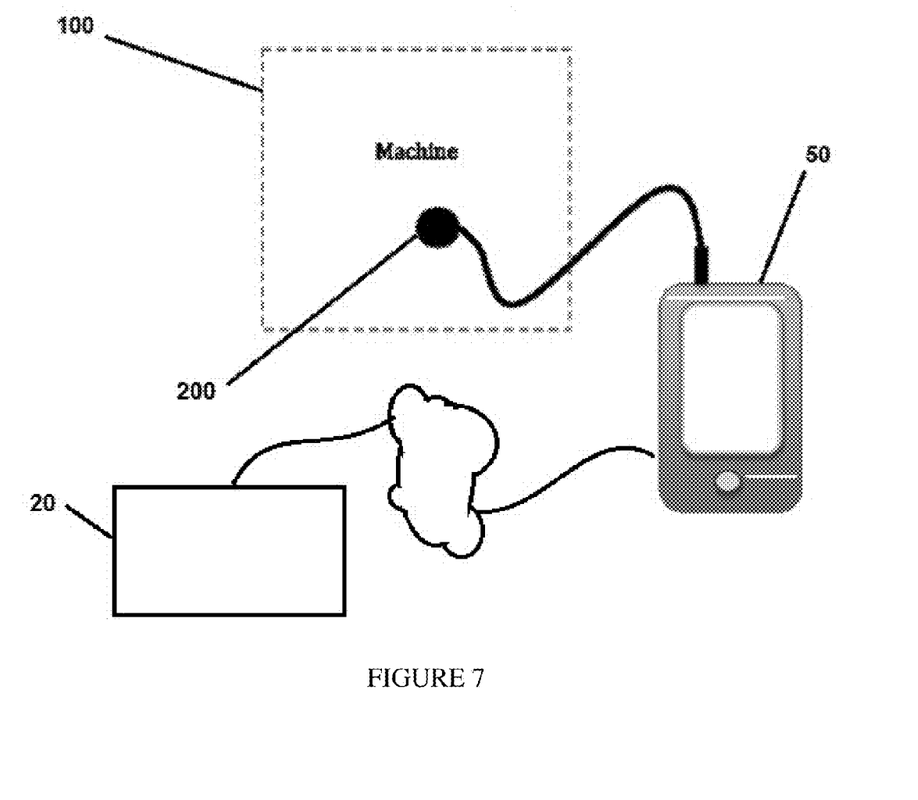
FIG. 7 is a drawing illustrating a mobile device with piezio electric transducer obtaining vibration signals from a machine.

By way of example and not limitation, referring to FIG. 7, in a second embodiment the system for measuring and analyzing a machine property comprises sensor 200 dimensioned and configured to sense vibration of structural component 100 with which sensor 200 is operatively in contact and terminal 50. Terminal 50 may be operatively in communication with system server 20 or, in other currently considered embodiments, process some or all data obtained from sensor 200 itself.

Figure 4:
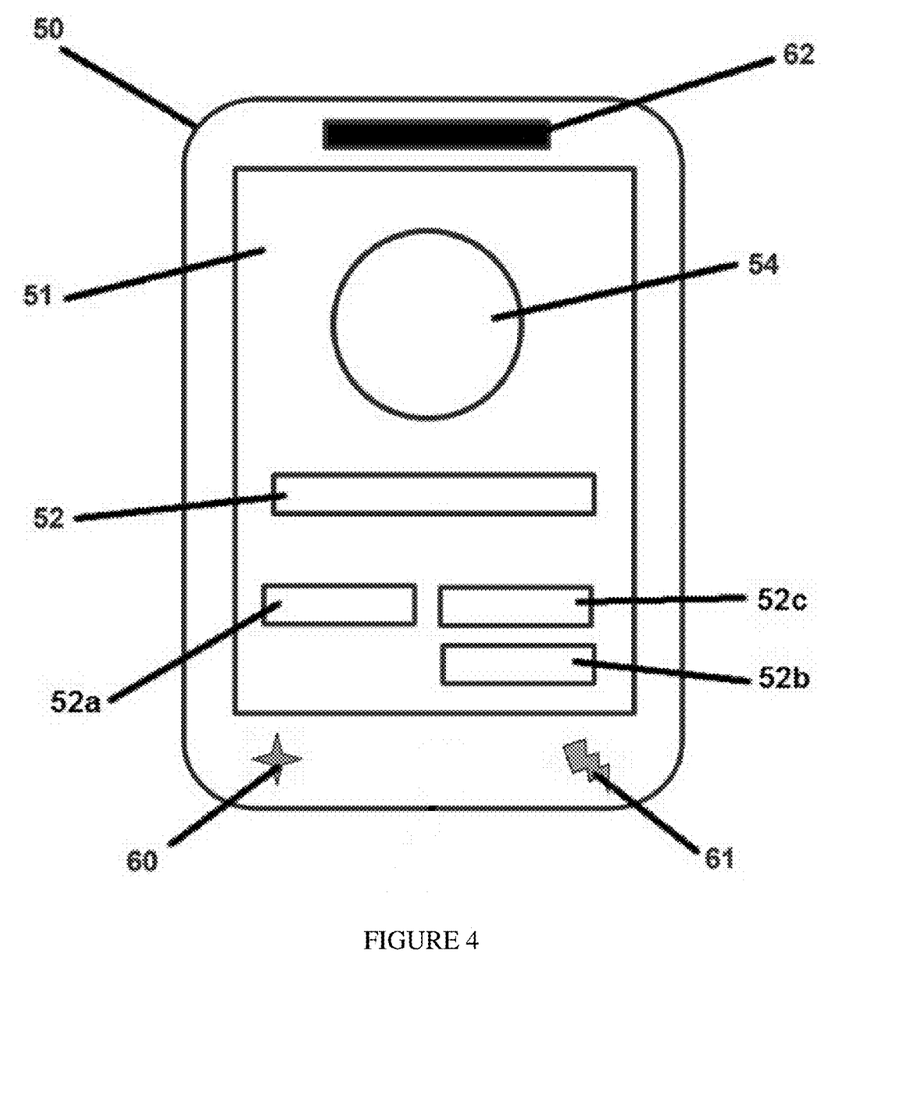
FIG. 4 is a screenshot illustrating the vibration capture screen on a mobile device.
Figure 5:
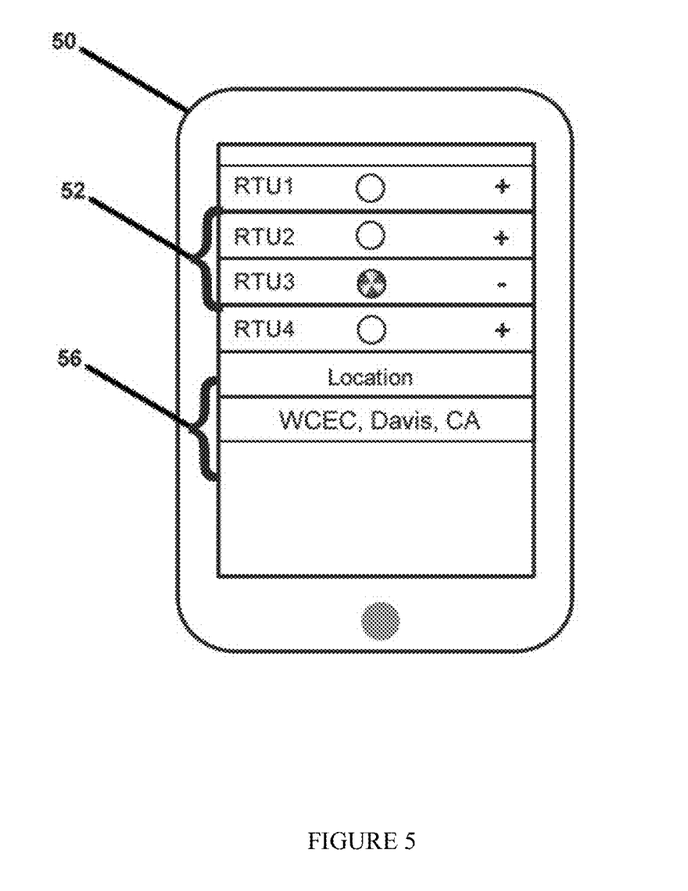
FIG. 5 is a screenshot illustrating the summary view on a mobile device.
Figure 6:
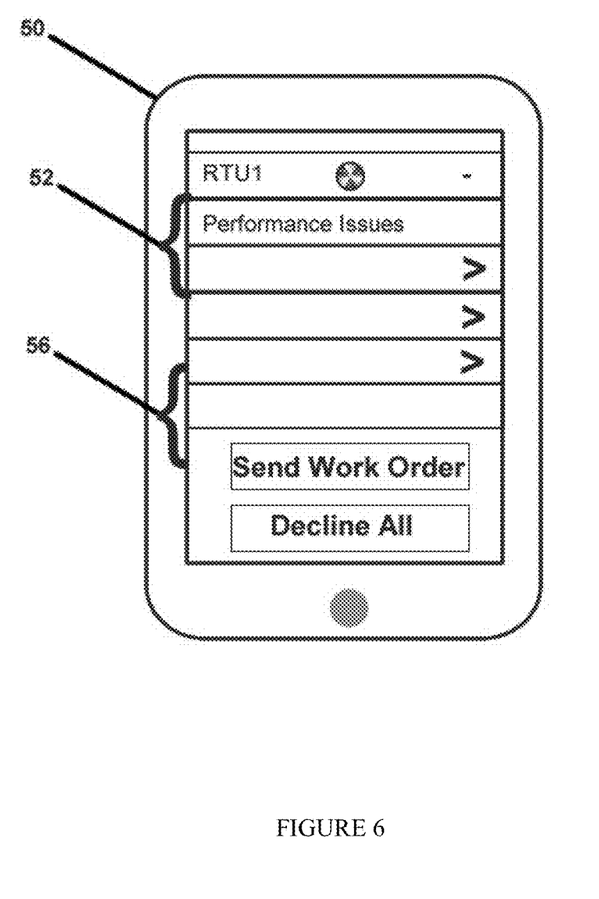
FIG. 6 is a screenshot illustrating the presentation layer on a mobile device.

Referring additionally to FIGS. 4-6, terminal 50 typically comprises power source 60, first data transceiver 61 operatively connected to power source 60; a user interface unit comprising user display area 52 which may further comprise user regions 52a-52c, one or more of which may comprise a user input area, e.g. 54; and first data processor 62 operatively connected to sensor 200, power source 60, user interface unit 51, and first data transceiver 61.

In this embodiment, first data processor 62 is configured and adapted to obtain sensed vibration data from sensor 200, either via a wired or wireless connection, and convert the vibration data into digital data. These data may be processed locally by first data processor 62, transmitted through first data transceiver 61 for processing, or a combination thereof. In addition, first data processor 62 may process the vibration and other data, either from local data, remote data, or a combination thereof, and can further include processing data for visual presentment on user display area 52. Some data, e.g. user input, may be obtained, e.g. from user input area 52e, and further processed by first data processor 62, system server 20, or a combination thereof.

Information provided by the above processes can be included in a presentation layer to the end user. The presentation layer can be delivered through a web browser, native device application, or any suitable application. The presentation layer may be located on the mobile device (FIG. 5 and FIG. 6), the embedded device, a computer, a thermostat, a device network/hardwire connected to terminal 1, or the like, or a combination thereof.

System server 20 is typically similar to system server 20 already described above and further typically comprises second data processor 22; second data transceiver 24 operatively connected to second data processor 22; and software operatively resident in second data processor 22. The software is typically configured to process and analyze data received via second data transceiver 24 where the received data comprises the sensed vibration data and/or user input. For clarity, although system server 20 is essentially identical to that described for the first embodiment herein, the "second" description is meant only to distinguish between its elements and those similar elements present in terminal 50.

In the operation of preferred embodiments, the system may be used to create timely notifications and easy-to-understand reports on a probable cause of a fault without the need for deep diagnostic or analytical expertise from an operator and associated expense. For example, the system enables non-technical people, for example a building owner, to discover inefficiencies with heating and air conditioning systems. Because the system is non-invasive, it can be installed to monitor less costly machinery at higher unit volumes making it economical to monitor and fix problems that cannot currently be discovered or addressed.

As described further below, a signal processing and analytics process is used to connect a vibration related signal with metadata and/or programmatic or device actions. In the context of this document, the term "vibration object" refers to a computer object form of a vibration signal. The linking of a vibration object applies to machines that are used in residential (e.g., refrigerators, heating/ventilation/air-conditioning (HVAC) systems), commercial (rooftop units (RTUs), chillers, fans, etc.), and/or industrial applications (generators, assembly lines, refining operations, etc).

Referring now to FIG. 3, in one embodiment, vibration data can be processed at least partially at a local device, e.g. detector 1 (FIG. 1) or and/or terminal 50 (FIGS. 1 and 7). Local signal processing can occur in real time or can be stored for processing on the local device at a later time. Local signal processing can extract, compress, and store relevant vibration information for transmission to a centralized signal processing server. Relevant vibration data outputs can include raw signal voltage, signal FFT, signal strength, decibel level, and signal patterns. This information is then used to determine machine performance. In addition to local signal processing, additional local information can be embedded into the vibration object (this can occur during centralized signal processing as well). Additional information can include, but is not limited to: GPS location, local realtime/historic climate data (temperature, wind direction/speed, humidity, weather etc), whole building/unit electric/natural gas measurements, inside space conditions and thermostat functions/history.

Processed and unprocessed vibration data can be transmitted to, e.g. system server 20, via the Internet. Transmission methods may include but are not limited to cell technology, wireless Internet, Ethernet, radio transmission, or the like, or a combination thereof. Data may be transferred as one packet of information or multiple packets of information.

Referring still to FIG. 3, in a first contemplated method a machine property, e.g. vibration, may be measured and by placing detector 1 (FIG. 1) into contact with structural component 100 (FIG. 1), where detector 1 is as described herein above. Vibration of structural component 100 is sensed, step 510, using sensor 6 (FIG. 1). At step 520, sensed vibration data are converted into digital data. At step 530, these digital data, along with any other data to be sent, are transmitted to system server 20 (FIG. 1), which is as described herein above. Software resident at system server 20 compares, at step 540, the digital data against a predetermined set of comparison data. In certain embodiments, a vibration object is used, at step 560, to model the sensed vibration, although other data processing techniques may be used to implement step 560. Based on the outcome of step 560, a reporting action may be initiated if the digital data meet a predetermined action threshold, including in real time or at predetermined intervals, e.g. monthly.

In certain embodiments, the software in system server 20 (FIG. 1) further comprises vibration analytics engine 230 (FIG. 1), which at step 560 includes modeling the digital data using the vibration analytics engine.

The digital data may be processed in system server 20 (FIG. 1) using constellation mapping, Fast Fourier Transform, a data integrity post processing technique, basic regression analysis, pattern recognition, Bayesian networks, numerical analysis methods, or the like, or a combination thereof.

System server data store 26 (FIG. 1) typically comprises historical vibration database 221 (FIG. 1), realtime vibration database 231 (FIG. 1), vibration fault library 211 (FIG. 1), or the like, or a combination thereof, and the digital data may be stored, at step 550, in historical vibration database 221, realtime vibration database 231, and/or vibration fault library 211.

For embodiments where system server 20 (FIG. 1) is paired with a locally processing terminal 50 (FIG. 7), second data processor 62 may be further adapted and configured to issue an operative command via an output transmission at step 570, e.g. via second data transceiver 64 to first data transceiver 61, and first data processor 62 may be further adapted and configured to respond to a received received operative command. In these configurations, the software in system server 20 may further comprise diagnostic software useful to diagnose a fault condition based on the compared digital data in the system server. If a fault is diagnosed, system server 20 may generate a command operative to effect a change to structural component 100 (FIG. 7) and send the command to detector 1, e.g. via second data transceiver 64 to first data transceiver 61. Once received at detector 1, detector 1 may then initiate an action in response to the received command.

The reporting action may comprise generating a report, issuing a command, issuing an alert, or the like, or a combination thereof. The reporting action may additionally comprise generating an output transmission at step 570. In addition, initiating of the reporting action may further comprise generating, at step 580, one or more descriptions of structural component 100 (FIG. 1). By way of example and not limitation, a first description may describe the digital data which meet the predetermined action threshold and a second description may describe an action to be taken based on the digital data which meet the predetermined action threshold. The second descriptions may also comprise economic data, a suggested action, location data, or the like, or a combination thereof, associated with structural component 100. These additional descriptions may be transmitted to and displayed at terminal 50 (FIG. 1).

The result report may include machine performance data such as run time, mean time to failure, component disaggregation, mechanical degradation, power efficiency, comparative data (similar machines, etc), mechanical fault probability, work order information, fault cost, or the like, or a combination thereof.

In certain embodiments, the result report information may also be integrated with a work order management system to be used by a maintenance contractor, facility manager or any suitable end user of the information.

A user may also initiate an action request, whether or not in response to a request from system server 20 (FIG. 1) and communicate the user action request to system server 20. This in turn may cause system server 20 to initiate a reporting action and/or issue a command to detector 1. By way of example and not limitation, a user may be presented, on user interface system 51 (FIG. 7), with a predetermined set of actions to be undertaken and select a desired action. This selection is transmitted to system server 20 which then receives the selection of one of the predetermined set of actions. Based on the received selection, system server 20 generates one or more commands operative to effect the selected action if the received selection is to perform the selected action and sends the one or more commands to detector 1. Once received at detector 1, the one or more commands trigger detector 1 to initiate an action) in response to the received command.

In certain embodiments, terminal 50 (FIG. 1) is located remotely from detector 50 and detector 1 (FIG. 1) and terminal 50 communicate wirelessly.

In a second contemplated method, one or more machine properties are measured and analyzed by placing sensor 200 (FIG. 7) into contact with structural component 100 (FIG. 7) and operatively connecting sensor 200 to terminal 50 (FIG. 7), where terminal 50 is as described herein above. A vibration property of structural component 100 is sensed at a predetermined interval and the sensed vibration converted into digital data by terminal 50. The converted data, along with other data as required, are transmitted to system server 20, which is as described above. Software resident in system server 20 compares the received data against a predetermined set of comparison data and the vibration data modeled in the vibration object. A reporting action is initiated if the data meet a predetermined action threshold. A result of the reporting action is sent to and displayed on the terminal user display area. This transmission to terminal 50 may be via the Internet, e.g. using cellular telephony technology, wireless transmission such as WiFi or Bluetooth®, wired methods such as Ethernet, and the like, or a combination thereof.

Figure 8:
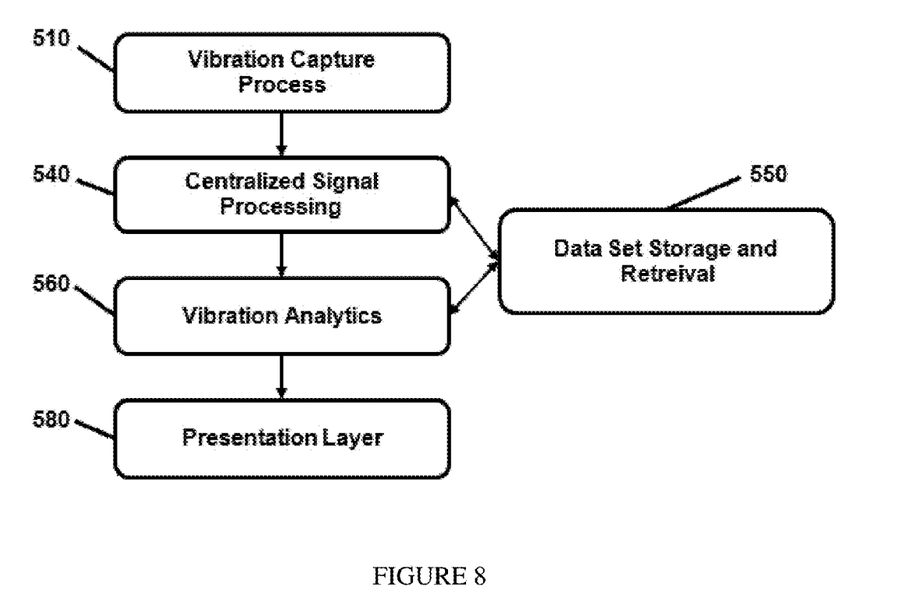
FIG. 8 is a flow diagram illustrating a complete vibration system that can be installed on a mobile device.

Referring to FIG. 8, in another contemplated method, a vibration system may be installed on a mobile device. Vibration of a structural component 100 is sensed, step 510, using sensor 6 (FIG. 1). Software resident at system server 20 compares, at step 540, the digital data against a predetermined set of comparison data. In certain embodiments, a vibration object is used, at step 560, to model the sensed vibration, although other data processing techniques may be used to implement step 560. Based on the outcome of step 560, a reporting action may be initiated if the digital data meet a predetermined action threshold, including in real time or at predetermined intervals, e.g. monthly. System server data store 26 (FIG. 1) typically comprises historical vibration database 221 (FIG. 1), real time vibration database 231 (FIG. 1), vibration fault library 211 (FIG. 1), or the like, or a combination thereof, and the digital data may be stored, at step 550, in historical vibration database 221, real time vibration database 231, and/or vibration fault library 211. The reporting action may comprise generating a report, issuing a command, issuing an alert, or the like, or a combination thereof. In addition, initiating of the reporting action may further comprise generating, at step 580, one or more descriptions of structural component 100 (FIG. 1).

Figure 9:
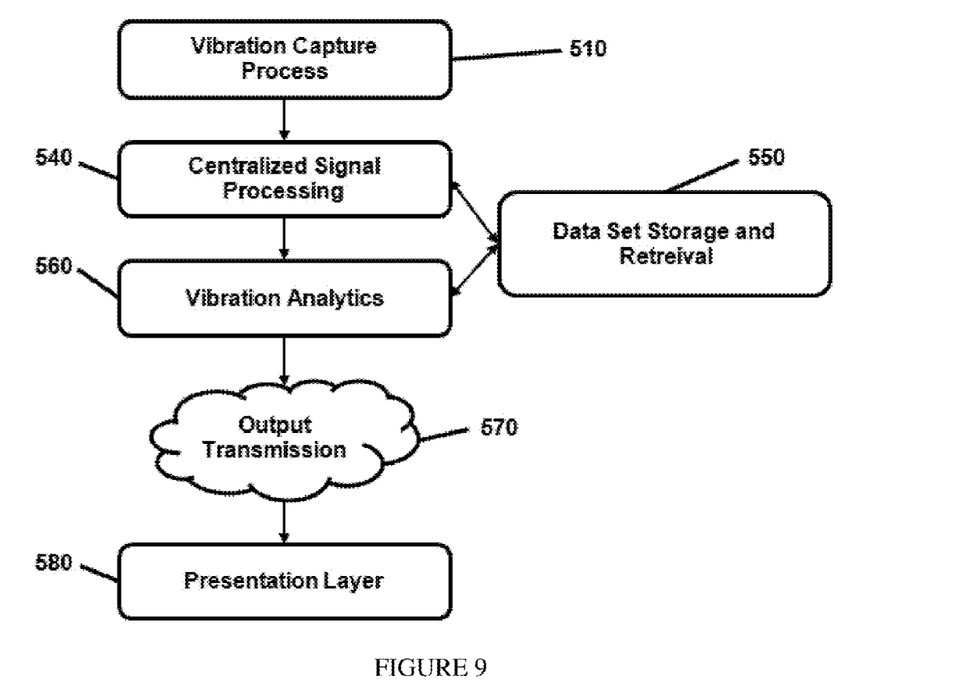
FIG. 9 is a block diagram illustrating an embodiment where a majority of processing occurs locally but is connected via the internet such that the output is remotely presented to the end user.

Referring to FIG. 9, in another contemplated method, an embodiment where a majority of processing occurs locally but is connected via the internet such that the output is remotely presented to the end user. Vibration of a structural component 100 is sensed, step 510, using sensor 6 (FIG. 1). Software resident at system server 20 compares, at step 540, the digital data against a predetermined set of comparison data. In certain embodiments, a vibration object is used, at step 560, to model the sensed vibration, although other data processing techniques may be used to implement step 560. Based on the outcome of step 560, a reporting action may be initiated if the digital data meet a predetermined action threshold, including in real time or at predetermined intervals, e.g. monthly. System server data store 26 (FIG. 1) typically comprises historical vibration database 221 (FIG. 1), real time vibration database 231 (FIG. 1), vibration fault library 211 (FIG. 1), or the like, or a combination thereof, and the digital data may be stored, at step 550, in historical vibration database 221, real time vibration database 231, and/or vibration fault library 211. The reporting action may comprise generating an output transmission at step 570. In addition, initiating of the reporting action may further comprise generating, at step 580, one or more descriptions of structural component 100 (FIG. 1).

Figure 10:
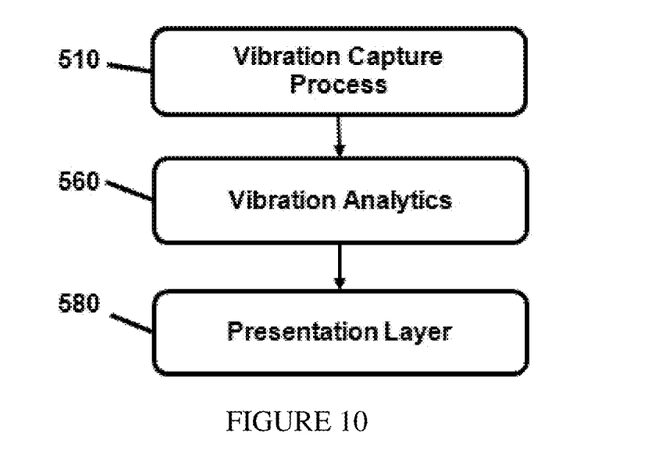
FIG. 10 is a flow diagram illustrating the process that provides the end user enabling performance data while removing one or more processes illustrated in FIG. 3.

Referring to FIG. 10, in another contemplated method, a process provides the end user enabling performance data without steps 510, 520, 530, 540, 550, and 570 as illustrated in FIG. 3. Vibration of a structural component 100 is sensed, step 510, using sensor 6 (FIG. 1). In certain embodiments, a vibration object is used, at step 560, to model the sensed vibration, although other data processing techniques may be used to implement step 560. Based on the outcome of step 560, a reporting action may be initiated if the digital data meet a predetermined action threshold, including in real time or at predetermined intervals, e.g. monthly. The reporting action may comprise generating a report, issuing a command, issuing an alert, or the like, or a combination thereof. In addition, initiating of the reporting action may further comprise generating, at step 580, one or more descriptions of structural component 100 (FIG. 1).

It may be desired to have sensor 6 installable or otherwise adjustable in the field. In embodiments comprising sensor assembly 70 (FIG. 11), sensor assembly 70 may be secured to structural component 100 (FIG. 1). As described described above, sensor 6 (FIG. 11) may have a predefined shape and sensor platform 71 (FIG. 11) may have void 74 that corresponds to the sensor predefined shape. In certain of these embodiments, sensor 6 is inserted into sensor assembly 70, e.g. sensor 6 is secured to or within sensor platform 71 as described below. It is noted that sensor assembly 70 may be connected or otherwise attached to structural component 100 before or after sensor 6 is secured to or within sensor platform 71, thereby allowing sensor 6 to be positioned and/or replaced in the field.

One or more guides 72 (FIG. 11) may be used to help position sensor 6 (FIG. 11) relative to structural component 100 (FIG. 1). In these embodiments, guide 72, which is connected to sensor platform 71 as described above, allows sensor 6 to be positioned relative to structural component 100 about axis 77 defined by guide 72. Sensor mount 73 (FIG. 11) may be adapted to selectively receive one or more guides 72 therethrough and be placed such that sensor 6 is located intermediate structural component 100 and sensor mount 73. Sensor cushion 75 (FIG. 11), as described above, is typically disposed intermediate sensor 6 and sensor mount 73 and may be placed on sensor 6 and/or sensor mount 73 before sensor 6 is secured into sensor assembly 70.

Once positioned, sensor 6 (FIG. 11) may be secured relative to sensor platform 71 (FIG. 11) by engaging sensor mount 73 (FIG. 11) against sensor 6 along axis 77. In certain embodiments, sensor cover 76 (FIG. 13) is dimensioned to selectively and, in certain embodiments, removably connect and be secured to guide 72 (FIG. 13), thereby further securing sensor 6 with respect to sensor assembly 70 and/or protecting detector 1 (FIG. 1) and its components. In these embodiments, sensor 6 may be selectively positioned relative to structural component 100 (FIG. 1) along axis 77 (FIG. 11) by adjusting sensor cover 76 and/or sensor mount 73 relative to guide 72 along axis 77.

For the sake of illustration, the disclosure focuses on a specific vibration object, vibration signals from a contact transducer attached to HVAC equipment (e.g., an RTU, chiller, fans, or the like). However, the system and its components and processes can also apply to other types of machine vibration signals, including residential, industrial and commercial equipment.

The foregoing disclosure and description of the inventions are illustrative and explanatory. Various changes in the size, shape, and materials, as well as in the details of the illustrative construction and/or an illustrative method may be made without departing from the spirit of the invention.

What is claimed is:

1. A system for measuring and analyzing a structural component property, comprising:
   a) a detector, the detector further comprising:
      i) a power source;
      ii) a sensor assembly, the sensor assembly comprising:
         (1) a sensor operatively connected to the power source, the sensor dimensioned and configured to sense a property of a structural component with which the sensor is operatively in contact;
         (2) a sensor platform dimensioned to selectively receive the sensor, the sensor platform configured to be secured to the structural component;
         (3) a sensor mount dimensioned to be received within the sensor assembly and engage the sensor; and
         (4) a guide connected to the sensor platform and dimensioned to selectively receive the sensor mount;
      iii) a data transmitter operatively connected to the power source; and
      iv) a first data processor operatively connected to the sensor, the power source, and the data transmitter, the first data processor configured and adapted to obtain sensed vibration data from the sensor and convert it into digital data to be transmitted through the data transmitter; and
   b) a system server operatively in communication with the detector, the system server further comprising:
      i) a second data processor;
      ii) a data receiver operatively connected to the second data processor; and
      iii) software operatively resident in the second data processor, the software dimensioned and configured to process and analyze data comprising the sensed vibration data received via the data receiver.

2. The system of claim 1, wherein the sensor assembly is configured to be substantially non-removably secured to the structural component.

3. The system of claim 1, wherein the sensor assembly is configured to be substantially removably secured to the structural component.

4. The system of claim 1, wherein the guide and sensor mount are configured to cooperatively guide the sensor within the sensor assembly.

5. The system of claim 1, wherein:
   a) the sensor comprises a predetermined exterior shape; and
   b) the sensor platform comprises a cooperatively shaped void configured to receive the sensor.

6. The system of claim 5, wherein the predetermined exterior shape comprises an outer circumference, a portion of which is substantially circular.

7. The system of claim 1, further comprising a cushion disposed intermediate the sensor and the sensor mount, the cushion configured to cushion the sensor relative to the sensor mount.

8. The system of claim 7, wherein the cushion comprises a foam.

9. The system of claim 1, wherein the guide comprises a post.

10. The system of claim 9, wherein the sensor mount further comprises a post annulus dimensioned to allow the post to pass through the post annulus.

11. The system of claim 1, wherein the sensor assembly further comprises a cover dimensioned to substantially cover the sensor, the cover adapted to connect to the sensor platform.

12. The system of claim 11, wherein the cover comprises a guide receiver dimensioned to receive the guide.

13. The system of claim 10, wherein the cover is configured to be secured to the guide using a selectively removable fastener.

14. A method for installing a system for measuring and analyzing a structural component property, comprising:
 a) inserting a sensor comprising a predefined shape into a detector, the sensor dimensioned and configured to sense vibration of a structural component with which the sensor is operatively in contact, the detector comprising:
  i) a power source;
  ii) a sensor assembly, the sensor assembly comprising:
   (1) a sensor platform, the sensor platform comprising:
    (a) a void corresponding to a predefined sensor shape; and
    (b) a guide; and
   (2) a sensor mount dimensioned to slidingly engage the guide;
  iii) a data transmitter operatively connected to the power source; and
  iv) a first data processor operatively connected to the sensor, the power source, and the data transmitter, the first data processor configured and adapted to obtain sensed vibration data from the sensor and convert it into digital data to be transmitted through the data transmitter;
 b) operatively connecting the sensor to the power source;
 c) securing the sensor within the sensor platform by placing the sensor intermediate the sensor platform and the sensor mount;
 d) placing the detector into contact with the structural component;
 e) positioning the sensor in a predetermined position relative to the structural component by adjusting the sensor mount along an axis defined by the guide to urge the sensor into the predetermined position;
 f) sensing the structural component's vibration using the sensor;
 g) converting the sensed vibration into digital data;
 h) transmitting the digital data to a system server, the system server comprising:
  i) a second data processor;
  ii) a data receiver operatively connected to the second data processor; and
  iii) software operatively resident in the second data processor, the software dimensioned and configured to process and analyze data comprising the sensed vibration data received via the data receiver, the software comprising a comparator, an analyzer, a vibration object, and a report initiator;
 i) comparing the digital data in the system server against a predetermined set of comparison data;
 j) modeling the sensed vibration in the vibration object; and
 k) initiating a reporting action if the digital data meet a predetermined action threshold.

15. The method of claim 14, further comprising disposing a sensor cushion intermediate the sensor and the sensor mount, the sensor cushion dimensioned to cushion the sensor with respect to the sensor mount when the sensor is secured into the sensor assembly.

16. The method of claim 14, further comprising:
 a) providing a plurality of guides connected to the sensor platform;
 b) positioning the sensor relative to the structural component about an axis defined by one of the guides; and
 c) securing the sensor relative to the sensor platform by engaging the sensor mount against the sensor along the axis.

17. The method of claim 14, further comprising:
 a) providing a sensor cover dimensioned to connect to the guide; and
 b) securing the sensor cover to the guide, thereby securing the sensor with respect to the sensor assembly.

18. The method of claim 17, wherein the sensor cover is selectively and removably secured to the guide.

19. The method of claim 18, further comprising selectively positioning the sensor relative to the structural component along the axis by adjusting the sensor cover relative to the guide along the axis.

* * * * *